US007550583B2

(12) United States Patent
Xia

(10) Patent No.: US 7,550,583 B2
(45) Date of Patent: Jun. 23, 2009

(54) METHOD OF ISOLATING, LABELING AND PROFILING SMALL RNAS

(75) Inventor: Xueliang Xia, Chandler, AZ (US)

(73) Assignee: Geno Sensor Corp., Tempe, AZ (US)

( * ) Notice: Subject to any disclaimer, the term of this patent is extended or adjusted under 35 U.S.C. 154(b) by 598 days.

(21) Appl. No.: 11/116,935

(22) Filed: Apr. 28, 2005

(65) Prior Publication Data

US 2006/0246464 A1 Nov. 2, 2006

Related U.S. Application Data

(60) Provisional application No. 60/650,034, filed on Feb. 4, 2005.

(51) Int. Cl.
*C07H 21/00* (2006.01)
*C07H 21/02* (2006.01)
(52) U.S. Cl. .................. 536/25.4; 536/23.1; 536/24.31
(58) Field of Classification Search .................. None
See application file for complete search history.

(56) References Cited

U.S. PATENT DOCUMENTS 4,582,789 A * 4/1986 Sheldon et al. ................ 435/6

OTHER PUBLICATIONS

England et al (Biochem. 17(11): 2069-2076, 1978).*
Igloi et al (Anal. Biochem. 233: 124-129, 1996).*
Aravin, Alexel A., et al., "The small RNA profile during *Drosophila melanogaster* development", *Developmental Cell 5*, (2003),337-350.
Calin, George A., et al., "Human microRNA genes are frequently located at fragile sites and genomic regions involved in cancers", *PNAS 101*, (2004),2999-3004.
Cheng, Jerry C., et al., "RNA interference and human disease", *Mol. Genetics Metab. 80*, (2003),121-128.
Gong, Huan, et al., "The role of small RNAs in human diseases: Potential troublemaker and therapeutic tools", *Medicinal Research Reviews*, (2004),1-14.
Hannon, Gregory J., et al., "Unlocking the potential of the human genome with RNA interference", *Nature 431*, (2004),371-378.
Kim, John, et al., "Identification of many microRNAs that copurify with polyribosomes in mammalian neurons", *PNAS 101*, (2004),360-365.
McManus, Michael T., "MicroRNAs and cancer", *Sem. Cancer Biol. 13*, (2003),253-258.
Ohtsuka, E et al., "Joining of 3'-modified oligonucleotides by T4 RNA ligase. Synthesis of a heptadecanucleotide corresponding to the bases 61-77 from *Escherichia coli* tRNAfMet.", *Biochemistry*, (Nov. 14, 1978), 4894-9, Abstract only.

Vratskikh, LV et al., "Solid-phase synthesis of oligoribonucleotides using T4 RNA ligase and T4 polynucleotide kinase.", *Biochimie*, (1995), 227-32, Abstract only.
Kikuchi, Y et al., "Addition of mononucleotides to oligoribonucleotide acceptors with T4 RNA ligase.", *Proceedings of the National Accademy of Sciences of the United Stated of America.* (Mar. 1978), 1270-3.
England, TE et al., "Enzymatic oligoribonucleotide syntheses with T4 RNA ligase", *Biochemistry*, (May 30, 1978), 2069-76, Abstract only.
Silverman, S K., "Practical and general synthesis of 5'-adenylated RNA (5'-AppRNA)". *RNA Journal*, (Apr. 2004), 731-46.
Wang, Y et al., "Efficient RNA 5'-adenylation by T4 DNA ligase to facilitate practical applications.", *RNA Journal*, (Jun. 2006), 1142-6.
Ohtsuka, E et al., "Joining of ribooligonucleotides with T4 RNA ligase and identification of the oligonucleotide-adenylate intermediate.", *Nucleic Acids Research*, (Jun. 1976), 1613-23.
McLaughlin, L W., et al., "Donor activation in the T4 RNA ligase reaction.", *Biochemistry*, (Jan. 15, 1985), 267-73, Abstract only.
Hoffmann, P U., et al., "Synthesis and reactivity of intermediates formed in the T4 RNA ligase reaction.", *Nucleic Acids Research*, (Jul. 10, 1987), 5289-303.
Walker, G C., et al., "T4-induced RNA ligase joins single-stranded oligoribonucleotides.", *Proceedings of the National Academy of Sciences of the United States of America.* (Jan. 1975), 122-6.

* cited by examiner

*Primary Examiner*—Richard Schnizer
(74) *Attorney, Agent, or Firm*—The Luther Law Firm, PC; Barbara J. Luther; William Sandals

(57) ABSTRACT

Disclosed herein is a method of selectively labeling non-messenger RNA molecules by isolating total RNA from a tissue or cell, dissolving the isolated RNA, blocking the 3' end of the RNA and adding T4 RNA ligase and a labeled nucleic acid adaptor. With the results that the T4 RNA ligase ligates the adaptor only to RNA having a 5' phosphate group and only small RNA are labeled. A method of labeling the 5' end of mRNA isolates total RNA from a tissue or cell, dissolving RNA in RNase-free water, removing a 5' cap structure from the mRNA using tobacco acid pyrophosphatase (TAP), removing the TAP, blocking the 3' end of the RNA molecules; and ligating an adaptor to the RNA by adding T4 RNA ligase and a labeled DNA or RNA adaptor. In another embodiment, there is disclosed a method of expression profiling small RNA by separating labeled RNA from capped RNA, providing a microarray comprising a plurality of probes hybridizable to small RNA, incubating the labeled small RNA with the microarray, washing unhybridized RNA from the microarray and drying the microarray, staining hybridized RNA on the microarray; and scanning the labeled microarray to determine the identity and quantity of labeling to the various miRNA probe sites and thus providing an expression profile of small RNA.

6 Claims, 4 Drawing Sheets

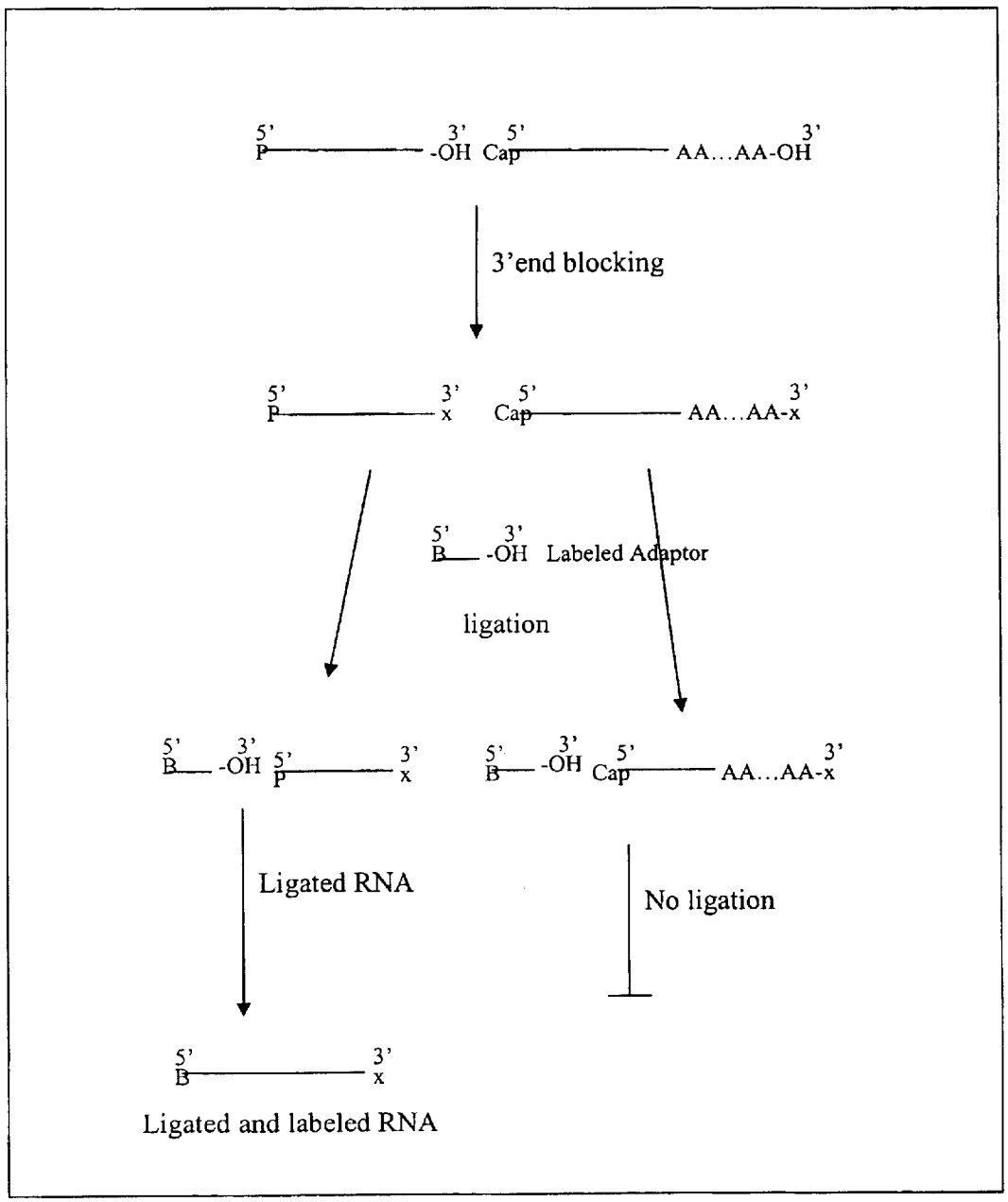

Fig 1. Schematic description of small RNA labeling. A. Block of the 3'–OH group. 3'–OH group of RNA is blocked by adding didexynucleotide using terminal transferase. B. Ligation of adaptors at 5' end. A labeled oligonucleotide adaptor is ligated using RNA ligase to the 5' end of uncapped RNA molecules including microRNAs, rRNAs, hnRNA, and other types of small RNA molecules. Capped mRNA cannot be ligated unless the 5' cap is removed.

A. Human Lymphoma

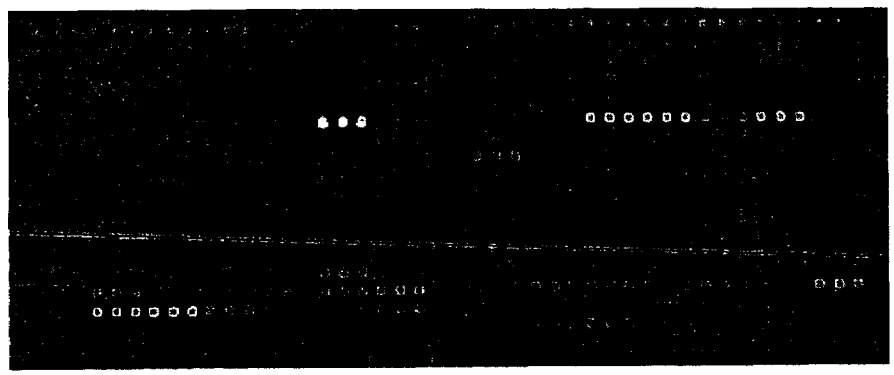

B. Human placenta

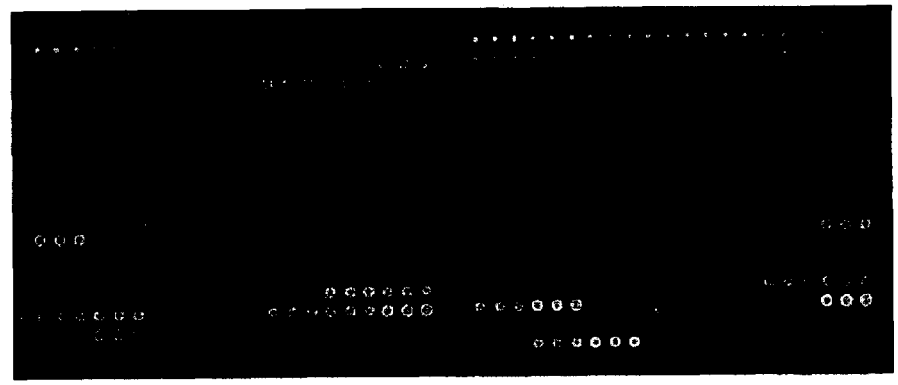

Fig 2. Examples of microRNA profiling on microarrays. Total RNA was isolated and labeled with biotinylated adaptors described as above. The labeled RNA samples were processed on microarray for hybridization. The arrays were scanned and the images of two tissues were shown above (A) human lymphoma and (B) placenta. Different patterns and differential expression of microRNAs were observed.

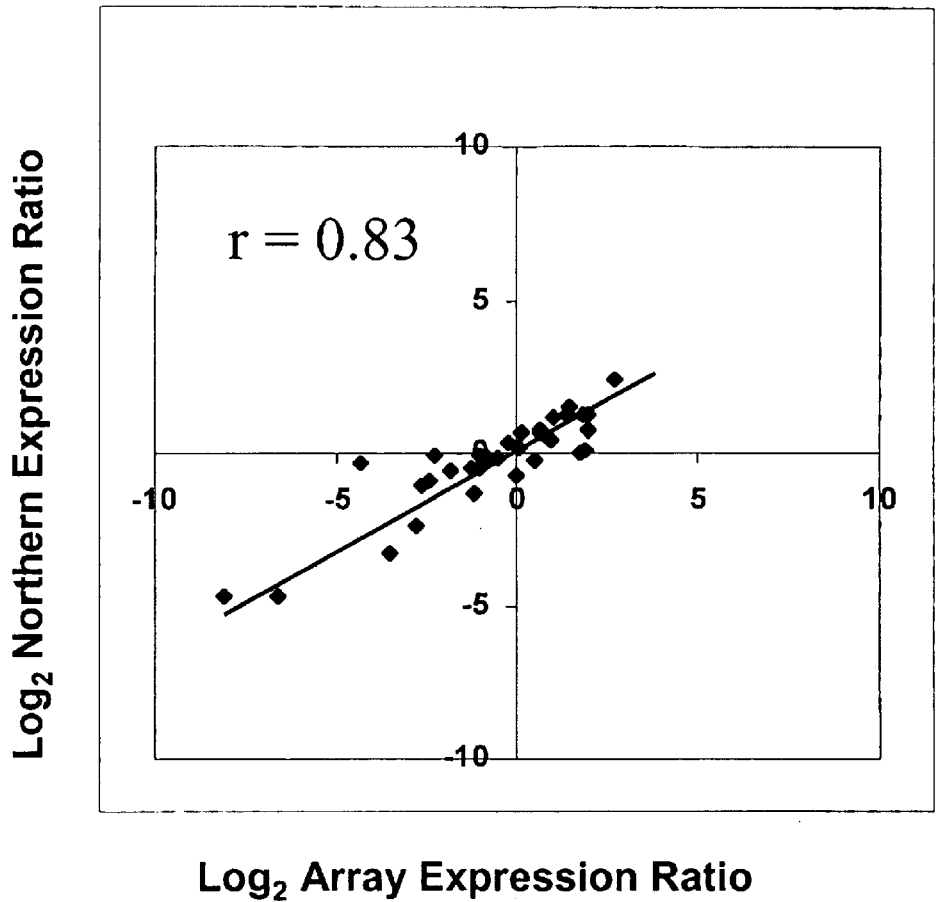
Fig 3. Northern blot assay was performed for the confirmation. Five miRNA probes (let-7b, miR-1b, miR-100, miR-125b, and miR128) were chosen to perform Northern blot. Expression levels were normalized log value was taken for the comparison plotting. The significant correlation ($p<0.05$) was observed with $r = 0.83$.

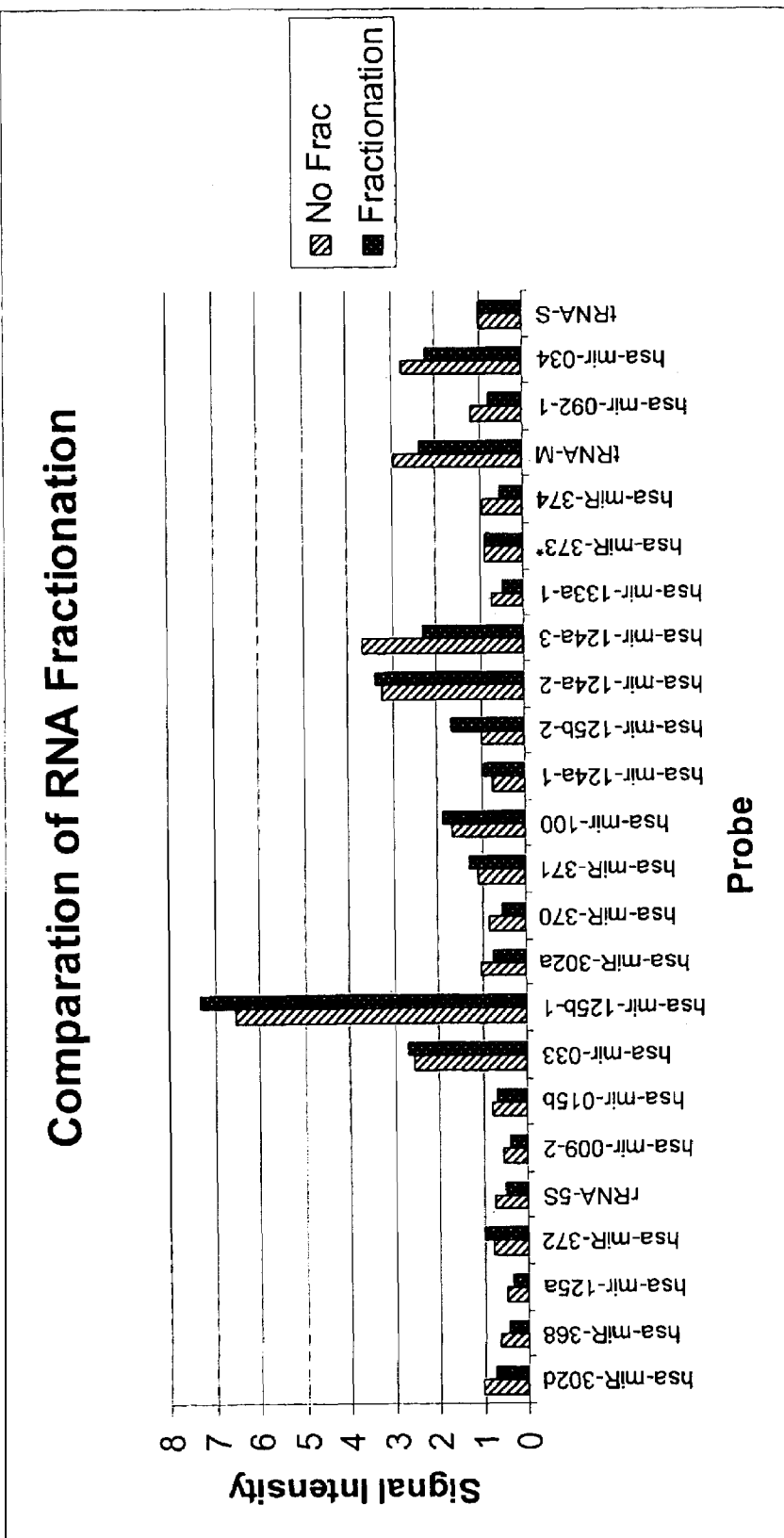
Fig 4. Comparison of RNA fractionation. Total RNA was isolated using Trizol method. The RNA was then either fractionated using size selection columns or no fractionation. No significant changes were observed on the signal numbers and intensity between use or no use of columns.

METHOD OF ISOLATING, LABELING AND PROFILING SMALL RNAS

CROSS REFERENCE TO RELATED APPLICATIONS

This application claims the benefit of prior-filed U.S. Provisional Application No. 60/650,034, filed Feb. 4, 2005.

TECHNICAL FIELD

The present invention relates generally to methods of analyzing small RNAs, and particularly to a method of isolating, labeling and profiling microRNAs.

BACKGROUND

The completion of Human Genome Project and genome sequencing on other species has had an enormous impact on human healthcare, quality of life, food, environment, and other living organisms. Sequencing of many other species is still ongoing. Now one of the major tasks is to understand the function and products of genomes. For a long time, there was a belief that RNA function was limited to their involvement in protein synthesis including messenger RNA, ribosomal RNA and transfer RNA (mRNA, rRNA, and tRNA, respectively). Recently identified small non-coding RNA molecules were discovered to be actively involved in gene regulation by directly interacting with mRNAs and silencing the genes, commonly referred to as RNA interference (RNAi). These RNA molecules are further classified into microRNAs (miRNAs) and small interference RNAs (siRNAs) and so on.

Although miRNAs play important roles in the regulation of gene expression, effective techniques for the detection and quantitation of miRNA expression are lacking. To date, the principal methods used for quantitation of miRNAs are based on gel electrophoresis. The miRNAs are detected either by Northern blotting or by the presence of radioactive RNase-resistant duplexes. Moreover, transfer of small RNAs to filters can introduce problems with reproducibility of quantitation and is not typically amenable to high-throughput. Moreover, detection methods based on Rnase resistance require highly radioactive probes. An alternative approach involves cloning the miRNAs and then sequencing the inserts. While this approach may be suitable for discriminating single-base differences between closely related miRNA species, it is time consuming and laborious.

The miRNAs and siRNAs are classes of small non-coding RNA molecules that are widely expressed in many cells and organisms, plants as well as animals. The mature forms of these RNAs are generally small (~22 nucleotides), the precursors of which are either hairpin or long double-stranded RNA (dsRNA) molecules transcribed from the genomes. These molecules are actively involved in gene regulation, RNAi and gene silencing, and important biological and pathological processes of cells. Profiling miRNA, siRNA and other types of small RNA expression in tissues and cells would greatly air understanding of these molecular functions and discovery of biomarkers for diagnostics and therapeutics.

Microarrays have been a powerful tool to profile gene expression, particularly mRNAs. However, profiling small RNAs on microarrays has not been validated. What is needed is an efficient way to analyze small RNAs in quantity.

SUMMARY OF THE INVENTION

Herein is described a method of profiling small RNA expression using microarrays. A new, specific method has been developed to perform this application. In this disclosure, miRNAs were used as an example for the method and application. Other types of RNAs can also be analyzed using variations on the disclosed method.

In one embodiment, there is a method of selectively labeling non-messenger RNA molecules by isolating total RNA from a tissue or cell, dissolving the isolated RNA, blocking the 3' end of the RNA and adding T4 RNA ligase and a labeled nucleic acid adaptor. With the result that the T4 RNA ligase ligates the adaptor only to RNA having a 5' phosphate group and only small RNA are labeled. Optionally, the isolated RNA is dissolved in RNase-free water. There can be an additional step of separating small RNA are separated from larger RNA, optionally on a gel or column. The labeled nucleic acid adaptor can be an oligonucleotide with interspersed label. The label may be biotin, a radioactive compound, a phosphorescent compound, or a fluorogenic compound. The biotin labeling is followed by treatment with streptavidin. The streptavidin can be streptavidin Alexa 647. The method has the step of blocking the 3' end of the RNA by reaction with dideoxynucleotide adenine (ddA) and terminal deoxynucleotidyltransferase (TdT). The miRNA or small RNA microarrays so produced can be used in genomic research, drug target validation, drug discovery, diagnostic biomarker identification or therapeutic assessment.

In another embodiment, there is disclosed a method of labeling the 5' end of mRNA that isolates total RNA from a tissue or cell, dissolves RNA in RNase-free water, removes a 5' cap structure from the mRNA using tobacco acid pyrophosphatase (TAP), removes the TAP, blocks the 3' end of the RNA molecules; and ligates an adaptor to the RNA by adding T4 RNA ligase and a labeled DNA or RNA adaptor. Optionally, the isolated RNA is dissolved in RNase-free water. Moreover, the small RNA can be separated from the larger RNA. The small RNA can be separated from the larger RNA on a gel or column. The labeled nucleic acid adaptor can be an oligonucleotide with interspersed label. The label can be biotin, a radioactive compound, a phosphorescent compound, or a fluorogenic compound. When the biotin labeling is used, it is followed by treatment with streptavidin. The streptavidin can be streptavidin Alexa 647. The 3' end of the RNA can be reacted with dideoxynucleotide adenine (ddA) and terminal deoxynucleotidyltransferase (TdT). The miRNA or small RNA microarrays so produced can be used in genomic research, drug target validation, drug discovery, diagnostic biomarker identification or therapeutic assessment.

In another embodiment, there is disclosed a method of expression profiling small RNA by separating labeled RNA from capped RNA, providing a microarray comprising a plurality of probes hybridizable to small RNA, incubating the labeled small RNA with the microarray, washing unhybridized RNA from the microarray and drying the microarray, processing post-hybridization RNA on the microarray, and scanning the labeled microarray to determine the identity and quantity of labeling to the various miRNA probe sites and thus providing an expression profile of small RNA. The miRNA or small RNA microarrays so produced can be used in genomic research, drug target validation, drug discovery, diagnostic biomarker identification or therapeutic assessment.

BRIEF DESCRIPTION OF THE DRAWINGS

FIG. 1 is a schematic depiction of the inventive method of small RNA labeling. Line 1 shows small RNA (left) and mRNA (right). After 3' end blocking, the second line shows both types of RNA are blocked (x at the 3' end). These blocked RNAs are then added to a labeled adaptor (B—OH), as shown in line 3. In line 4 only the small RNA with a phosphate at the 5' end can be ligated to the adaptor; there is no ligation of the other mRNA species.

FIGS. 2A and 2B are examples of miRNAs profiled on microarrays. Total RNA was isolated and labeled with biotinylated adaptors as outlined in FIG. 1. The labeled RNA samples were processed on microarrays for hybridization. The arrays were scanned and the images of two tissue samples shown above were for human lymphoma (2A) and placenta (2B). The different patterns in FIGS. 2A and 2B illustrate differential expression of miRNAs for the two exemplary tissues.

FIG. 3 is a graph derived from a Northern blot assay for confirmation of microarray information. Five miRNA probes (let-7b, miR-1b, miR-125b and miR-128) were chosen for use in the Northern blot. Expression levels were normalized log values taken for comparison plotting. The significant correlation ($p<0.05$) was observed with $r=0.83$.

FIG. 4 is a bar graph showing results with (solid bars) and without (bars with diagonal lines) RNA fraction, a method commonly used to study small RNA. Total RNA was first isolated using the Trizol method. Then RNA was either fractionated using size selection columns or was not fractionated. No significant changes were observed in the signal numbers and intensity between the paired columns.

DETAILED DESCRIPTION

This invention provides a method to profile small RNA molecules including microRNAs in cells, tissues and organisms. The specific technical platform used herein was microarrays, because microarrays afford a powerful system for massive and parallel detection of hundreds and even thousands of targets at the same time. Microarrays have been become a common tool for functional genomic and molecular profiling.

MicroRNAs and other small non-coding RNAs, unlike mRNAs, have a phosphate group at their 5' end and no 5' structural modification (or 5' cap). This phosphate provides a functional group to covalently bond to an —OH group at the 3' end of an oligonucleotide adaptor. RNA ligase connects two molecules between the 5' phosphate group on the RNA molecule and 3'-OH group of adaptors (FIG. 1). This method provides many advantages.

The first and foremost advantage of this method is selective labeling. All RNA molecules have 3'-OH groups. Whereas, two types of structures are identified at the 5' ends of RNA: the 5' cap for mRNA and a 5' phosphate group for small RNA molecules. Thus, ligation only labels small RNA with 5' phosphate groups, providing a means for selective labeling, thereby reducing labeled species complexity.

The second advantage owes its benefit to the fact that T4 RNA ligase can ligate RNA to single-stranded DNA/RNA oligonucleotide adaptors. In this invention, the adaptors are single-stranded DNA oligos labeled with biotin molecules at both 5' end and an internal location. Instead of DNA oligos, the adaptors can be composed entirely or partly of RNA molecules. Besides biotin, many other dye molecules can be used, including but not limited to fluorescent dyes and enzymatic substrates, etc.

To avoid sample RNA binding to sample RNA, the 3'-OH of RNA must be blocked before ligation. Herein were used dideoxynucleotide adenine (ddA) and terminal deoxynucleotidyltransferase (TdT) to block all 3'-OH groups of RNA; other hydroxyl blockers are well known in the art.

Third, this method of labeling ensures good labeling ratio and efficiency between targets and adaptors, reducing the differential and bias labeling that most chemical and UV cross-linking methods create.

Microarrays generally consist of a substrate matrix and nucleotide probes. Organic polymers or treated glass are used for a matrix that is supportive and biocompatible. Frequently, polymer chemistry modifications are used for better nucleotide probe attachment. The attached nucleotide probes are designed to hybridize target sequences. The attached nucleotide probes are antisense probes and are printed or otherwise spotted on the matrix and immobilized on the arrays. Nucleotide probes can also be photolithosynthesized in situ on the arrays.

DNA probes on the microarrays were used in the experiments for miRNA detection. The probe sequences were antisense of miRNAs. The probes were designed for optimal temperature/salt concentrations as well as hybridization properties. The probes were printed on the arrays. To determine whether the microarray technique were robust, 210 probes were designed and printed on several microarrays.

As used herein, the terms "complementary" or "complementarity" are used in reference to polynucleotides (i.e., a sequence of nucleotides such as an oligonucleotide or a target nucleic acid) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in detection methods that depend upon binding between nucleic acids. Either term may also be used in reference to individual nucleotides, especially within the context of oligonucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The detected materials are RNA that has been isolated from cells or tissues. The invention does not depend on the method of harvesting the RNA. Any accepted method for harvesting RNA can be used, including but not limited to, phenol/chloroform separation, as well as commercial kits and columns, such as the TRIZOL reagent (Invitrogen). The harvested RNA that is detected can be, but need not be, total RNA or size-selected RNA.

Subsequently the harvested small RNA was labeled for further analysis. Total RNA, fractionated RNA, or other types of treated RNAs can be labeled according to the same principle. In this invention, the label is part of a signaling oligonucleotide that chemically combines with the 5' phosphate end of short RNA. Herein, the signaling oligonucleotide carries a biotin molecule, preferably two biotins, one in the center and one at its 5' end, so as not to obstruct or be obstructed by the small RNA hybridizing to the microarray.

A variety of signals can be incorporated into the signaling oligonucleotide. These include, but are not limited to, radioactive compounds (including but not limited to $p^{32}$, $p^{33}$, $S^{35}$, $I^{125}$ and $I^{131}$ or others known in the art or discovered in the future). Additional alternative labels include, but are not limited to, dyes; binding moieties such as biotin; haptens such as digoxigenin; luminogenic, phosphorescent or fluorogenic moieties; mass tags; and fluorescent dyes alone or in combination with moieties that can suppress or shift emission spectra by fluorescence resonance energy transfer (FRET); and enzymatic substrates. Labels may provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry; fluorescence polarization), and the like. A label may be a charged moiety (positive or negative charge) or alternatively, may be charge neutral. Adaptors can include or consist of nucleic acid or protein sequences, so long as the sequence comprising the label is detectable.

Certain nucleotide bases not commonly found in natural nucleic acids may be included in the nucleic acid adaptor or in the probe attached to the microarrays of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

In addition, "nucleotide analogs" as used herein refers to modified or non-naturally occurring nucleotides including, but not limited to, analogs that have altered stacking interactions such as 7-deaza purines (i.e., 7-deaza-dATP and 7-deaza-dGTP); base analogs with alternative hydrogen bonding configurations (e.g., such as Iso-C and Iso-G and other non-standard base pairs described in U.S. Pat. No. 6,001,983 to S. Benner and herein incorporated by reference); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872; each of which is herein incorporated by reference); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogs include nucleotides having modification on the sugar moiety, such as dideoxy nucleotides and 2'-O-methyl nucleotides. Nucleotide analogs include modified forms of deoxyribo-nucleotides as well as ribonucleotides.

Biological samples may be animal, including human (normal or abnormal), fluid, solid (e.g., stool) or tissue, as well as liquid and solid food and feed products and ingredients such as dairy items, vegetables, meat and meat by-products, and waste. Biological samples may be obtained from eukaryotic organisms such as yeasts, plants and animals, including but not limited to all of the various families of domestic animals, as well as feral or wild animals, including, but not limited to, such animals as birds, ungulates, bear, fish, lagomorphs, rodents, etc. Fungi, yeasts, bacteria, viruses and prions also can be sampled.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

This inventive method of labeling small RNA can be used in genomic research, drug target validation, drug discovery, diagnostic biomarker identification or therapeutic assessment.

This method can be adapted for the labeling of the 5' end of mRNAs. If on examination of the miRNA, examination of mRNAs is needed, the 5' cap can be removed from the mRNA. The decapitating step can be inserted between before line 1 in FIG. 1 or lines 1 and 2. One unit of tobacco acid pyrophosphatase (TAP) is used at 37° C. for one hour to remove the 5' cap from the mRNA molecules and followed by phenol/chloroform purification, the decapped samples can be processed to line 1 of line 2.

RNA can be isolated by any methodologies, such as well known phenol/chloroform method, commercial kits and columns. Isolated total RNA was dissolved in RNase-free water for the labeling protocol described above.

Profiling methodology described here is microarray biochips. Detection probes on the microarray are complementary to detected RNA, and detected miRNA has been directly labeled. The probes are designed based on the RNA sequences. The microarrays with miRNA probes were manufactured using OmniGrid Arrayers. The probes were DNA oligos with 30 nt long, complementary to the miRNA mature sequences. Labeled RNA hybridizes with probes on the arrays. The signal intensity of all probes are scanned and analyzed.

To summarize and based on FIG. 1, the 3'-OH of RNA was blocked by dideoxynucleotide adenine (ddA; Amersham) using terminal deoxynucleotidyltransferase (TdT; New England Biolab). Instead of ddA ddT, ddG or ddC may be used. Once the 3' end of the RNA has been blocked, small RNA are molecularly ligated to a labeled adaptor, such as 5' biotin-AAAAAAAAAAAAAAA-biotin-AAAAA-3' (SEQ ID NO. 1). Other natural nucleotides as well as synthetic nucleotides can be used, as discussed above. The length of the oligonucleotide can be varied from 1 to hundresd), as can the number of signaling compounds in the labeled adaptor, for example, from one to ten, 20, 30, 40 or more. Those skilled in the art can optimize the oligo adaptor length as well as the signaling moiety. Signaling moiety size would be limited by cost and/or quenching and other factors. To label the small RNA, the adaptors and T4 RNA ligase were added to the blocked RNA solution to produce.

The hybridization conditions and temperature typically depend on the types of microarrays and length of array probes. In these miRNAs experiments, the microarray probes were about 30 nt long, and sequences were designed based on and complementary to known miRNA sequences. With added formamide and SSPE (or SSC) buffer, the hybridization on the array chips took place overnight. Timing and temperature can be optimized by those of skill in the art, after seeing the following examples. After incubation, the arrays are washed and stained with a variety of dyes, depending on the Adaptor label. With biotin, streptavidin Alexa 647 (Molecular Probes) was used. After washing repeatedly and allowing to dry, the microarrays were scanned, the signal intensity of all probes was recorded and computed. The miRNA expression profiling for the samples were analyzed and compared with other microarray results.

Following are examples using total and fractionated RNA.

EXAMPLE 1

This experiment includes total RNA isolation, RNA labeling, microarray hybridization, array scanning and data analysis for profiling. See FIG. 1 for detailed steps.

Total RNA was isolated from 8 tissues or cells (liver, kidney, lungs, placenta, testis, prostate and lymphoma) using the phenol and chloroform method, or TRIZOL reagent (Invitrogen). The obtained RNA was dissolved in RNase-free water.

Five micrograms of total RNA was used. If total RNA is used, it is preferable to use about 10 μg; whereas, if fractionated miRNA is used, amounts as low as 0.5 μg can be used.

3' end blocking. 10 μg of total RNA, 1 nmol ddA, 50 mM K Acetate (Ac), 20 mM Tris buffer with acetate (pH 7.9), 10 mM MgAc$_2$, 1 mM dtt, 0.25 mM CoCl$_2$, 6.7% DMSO (Sigma), 4 units of TdT in a final volume of 15 μg. One nmol dideoxynucleotide adenine (ddA) and 4 units of terminal deoxynucleotidyl-transferase (TdT) were added in 5 μg of total RNA samples to make a volume of 10 μl. The reaction was performed at 37° C. for an hour, then heated up to 70° C. for 20 minutes to inactivate the TdT. Thus, the 3'-OH groups were blocked by attachment of ddA. This step prevents miRNA intermolecular ligation at the next step.

Ligation. A biotin-labeled DNA adaptor was used for the ligation. 500 pmol adaptors (wherein the adaptor consisted of an oligonucleotide consisting of 20 adenine residues with one biotin moieties at the 5' end, and another between the 15$^{th}$ and 16$^{th}$ residues) and 5 units of T4 RNA ligase (New England Bioscience) were added to the previously blocked RNA solution. In addition, a ligation buffer was added to a final concentration of 40 mM tris-Ac (pH 7.9), 37 mM KAc, 10 mM MgCl$_2$, 3.5 mM DTT, 0.25 ATP, 0.18 CoCl$_2$, 10% DMSO and 5 mg/mL bovine serum albumin (BSA). The reaction was performed at 4° C. for 2 hr (although the temperature and time can be varied). Then the solution was heated and maintained at 65° C. for 15 minutes to inactivate the ligase.

Storage or microarray hybridization. Labeled RNA samples can be stored frozen at −70° C. (or lower) or directly applied to the microarray. The hybridization condition and temperature depends on types of microarrays and length of array probes. In this miRNA case, the miRNA probes were 30 nt long and sequences were designed to be complementary to the miRNA sequences. With 30% formamide (can be varied between 10 and 50%) and 6× SSPE buffer (optionally SSC), the hybridization on the array chips was maintained at 30° C. for 16 hr or overnight.

The arrays were washed and stained with streptavidin-Alexa dyes (Genisphere), Customary buffers were used for washing, including 1× SSC with 0.1% SDS, and then 0.2× SSC at 37 C. Final washes were in water. After the arrays dried, they were scanned by a scanner. The signal intensities of all probes on the arrays were recorded and computed. The miRNA expression profiling for the samples were analyzed. The results for lymphoma and placenta are shown as FIG. 2A and FIG. 2B, respectively. The patterns of miRNAs in these tissues were markedly different.

EXAMPLE 2

Five miRNAs were selected for the comparison of this inventive labeling method on microarrays with the standard Northern blot method. The DNA probes (the same sequences as on the arrays) used for the Northern were radioactively labeled (P$^{33}$) and the Northern method was performed on the eight human tissues mentioned above. The result shows a significant correlation ($p<0.05$) between the array results using the described method on microarrays and on Northern blot (FIG. 3).

EXAMPLE 3

Fractionated RNA samples were also tested. RNA was isolated from three different cell lines using Invitrogen MyRNA kit, or a similar kit from Ambion, to enrich for small RNA molecules. As described above, only 0.5 μg of fractionated RNA was used for labeling. The labeled RNA was then used for hybridization on the arrays. The results were used to compare with total RNA experiments isolated from the same tissues (FIG. 4). The signal patterns and intensity significantly correlated, suggesting the efficiency of labeling.

EXAMPLE 4

If examination of 5' end of mRNAs is needed, then labeling of 5' end mRNA becomes necessary. The above methodology can be used for this application. One additional step is needed to remove the 5' cap structure from mRNA. The "decap" step can be inserted between steps 1 and 2, or between steps 2 and 3. To remove the 5' cap from the mRNA, the mRNA was exposed to 1 unit of tobacco acid pyrophosphatase (TAP) at 37° C. for 1 hr. Followed by phenol/chloroform purification, the decapped samples can be processed as in step 2 or step 3.

This new method of miRNA profiling on microarrays provides a high-throughput tool for genomic research, target validation, and identification of biomarkers. The labeling methodology efficiently labels miRNAs and other non-capped RNA molecules. The method also is adaptable to capped RNA molecules. The 5' end of RNA molecules can be labeled using adaptors by ligation and can be applied to the following molecules: microRNAs, siRNAs and other small RNAs, any RNAs without 5' caps, and mRNAs after 5' decapping.

This method of selective labeling of RNA species can be used in many technology platforms, including but not limited to microarray analysis and northern blot analysis.

The method of applying 5' labeled RNA to microarrays will be useful in numerous ways, such as genomic research, drug target validation, drug discovery, diagnostic biomarker identification and therapeutic assessment.

While the foregoing specification discloses how to use and make the invention, the specification is not to be used to define the invention, which is the province of the claims.

The invention claim is:

1. A method of selectively labeling non-messenger RNA molecules, the method comprising
   a. isolating total RNA from a tissue or cell;
   b. dissolving the isolated total RNA to form a solution of dissolved RNA molecules;
   c. blocking 3' ends of the dissolved RNA molecules; and
   d. adding T4 RNA ligase and a labeled nucleic acid adaptor whereby the T4 RNA ligase ligates the adaptor only to RNA molecules having a 5' phosphate group and only non-messenger RNA molecules are labeled.

2. The method of claim 1, wherein after step b, the RNA molecules are fractionated by size.

3. The method of claim 2, wherein the RNA molecules are fractionated on a gel or column.

4. The method of claim 1, wherein in step d, the label is selected from biotin, a radioactive compound, a phosphorescent compound, or a fluorogenic compound.

5. The method of claim 4, wherein the biotin labeling is used, with streptavidin.

6. The method of claim 1, wherein in step c, the 3' ends of the RNA molecules are reacted with dideoxynucleotide adenine (ddA) and terminal deoxynucleotidyltransferase (TdT).

* * * * *